(12) United States Patent
Yan et al.

(10) Patent No.: US 9,511,243 B2
(45) Date of Patent: Dec. 6, 2016

(54) PREVENTION OF SETUP ERRORS IN RADIOTHERAPY

(71) Applicant: University of Florida Research Foundation, Inc., Gainesville, FL (US)

(72) Inventors: Guanghua Yan, Gainesville, FL (US); Bo Lu, Gainesville, FL (US); Chihray Liu, Gainesville, FL (US); Jonathan G. Li, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 247 days.

(21) Appl. No.: 14/394,357

(22) PCT Filed: Apr. 12, 2013

(86) PCT No.: PCT/US2013/036340
§ 371 (c)(1),
(2) Date: Oct. 14, 2014

(87) PCT Pub. No.: WO2013/155394
PCT Pub. Date: Oct. 17, 2013

(65) Prior Publication Data
US 2015/0126796 A1    May 7, 2015

Related U.S. Application Data

(60) Provisional application No. 61/623,395, filed on Apr. 12, 2012.

(51) Int. Cl.
*A61N 5/10* (2006.01)
*A61B 6/03* (2006.01)
(Continued)

(52) U.S. Cl.
CPC ............... *A61N 5/1048* (2013.01); *A61B 6/03* (2013.01); *A61B 6/583* (2013.01); *A61N 5/107* (2013.01);
(Continued)

(58) Field of Classification Search
CPC .. A61N 5/1048; A61N 5/1049; A61N 5/1064; A61N 5/1067; A61N 5/1069; A61N 5/107; A61N 2005/105; A61N 2005/1051; A61N 2005/1059; A61N 2005/1063
See application file for complete search history.

(56) References Cited

U.S. PATENT DOCUMENTS 6,279,579 B1    8/2001 Riaziat et al.
6,490,473 B1   12/2002 Katznelson et al.
(Continued)

FOREIGN PATENT DOCUMENTS

EP    2377576       10/2011
FR    2946243 A1 * 12/2010 ........... A61N 5/1049
WO   99/30182        6/1999

OTHER PUBLICATIONS

Translation of the French patent publication by EPO and Google.*
(Continued)

*Primary Examiner* — Charles A Marmor, II
*Assistant Examiner* — Thaddeus Cox
(74) *Attorney, Agent, or Firm* — Jon Gibbons; Fleit Gibbons Gutman Bongini & Bianco P.L.

(57) ABSTRACT

A patient safety system (PSS) (100) uses optical tracking in a linear accelerator treatment room to prevent gross setup errors. A patient (150) undergoes a computed tomography (CT) treatment-simulation scan while a CT ball bearing (BB) is on patient's surface. The CT BB is replaced with an infrared reflective marker (IRRM) (160) before radiotherapy treatment starts. Coordinates of the CT BB relative to an
(Continued)

isocenter of the treatment room are used as reference for tracking. The coordinate system of an optical tracking system is converted to a coordinate system of the treatment room. The PSS evaluates setup accuracy for a radiotherapy session by comparing real-time position of the single IRRM determined by the optical tracking technology with a predicted reference position, and displays results on a graphical user interface. The PSS stops radiation when a deviation between real-time coordinates and predicted coordinates of the IRRM (160) exceeds a predefined threshold.

20 Claims, 4 Drawing Sheets

(51) Int. Cl.
| | | |
|---|---|---|
| *G01S 17/48* | (2006.01) | |
| *G01S 17/66* | (2006.01) | |
| *G01S 17/87* | (2006.01) | |
| *A61B 6/00* | (2006.01) | |
| *G01B 11/25* | (2006.01) | |
| *H04N 13/00* | (2006.01) | |

(52) U.S. Cl.
CPC .......... *A61N 5/1049* (2013.01); *G01B 11/254* (2013.01); *G01S 17/48* (2013.01); *G01S 17/66* (2013.01); *G01S 17/87* (2013.01); *H04N 13/0048* (2013.01); *A61N 2005/1051* (2013.01); *A61N 2005/1059* (2013.01); *A61N 2005/1074* (2013.01)

(56) References Cited

U.S. PATENT DOCUMENTS

| | | |
|---|---|---|
| 6,535,574 B1 | 3/2003 | Collins et al. |
| 6,775,404 B1 | 8/2004 | Pagoulatos et al. |
| 7,024,237 B1 | 4/2006 | Bova et al. |
| 7,204,254 B2 | 4/2007 | Riaziat et al. |
| 7,535,411 B2 | 5/2009 | Falco |
| 7,657,303 B2 | 2/2010 | Mate et al. |
| 7,715,606 B2 | 5/2010 | Jeung et al. |
| 7,729,472 B2 | 6/2010 | Scherch et al. |
| 7,881,767 B2 | 2/2011 | Strommer et al. |
| 2002/0044204 A1 | 4/2002 | Zurl et al. |
| 2004/0138556 A1 | 7/2004 | Cosman |
| 2004/0158146 A1 | 8/2004 | Mate et al. |
| 2005/0117708 A1* | 6/2005 | Cho ................ A61B 6/547 378/164 |
| 2006/0215813 A1 | 9/2006 | Scherch et al. |
| 2007/0287911 A1 | 12/2007 | Haid et al. |
| 2008/0033283 A1 | 2/2008 | Dellaca et al. |
| 2008/0095416 A1 | 4/2008 | Jeung et al. |
| 2008/0132785 A1 | 6/2008 | Piron et al. |
| 2008/0287728 A1 | 11/2008 | Mostafavi et al. |
| 2008/0287783 A1 | 11/2008 | Anderson |
| 2008/0317313 A1 | 12/2008 | Goddard et al. |
| 2009/0039886 A1 | 2/2009 | White |
| 2009/0088622 A1 | 4/2009 | Mostafavi |
| 2010/0008467 A1 | 1/2010 | Dussault et al. |
| 2011/0230755 A1 | 9/2011 | MacFarlane et al. |
| 2011/0306863 A1 | 12/2011 | Koshnitsky et al. |

OTHER PUBLICATIONS

International Search Report and Written Opinion dated Aug. 29, 2013, received for PCT Application No. PCT/US2013/036331.

International Preliminary Report on Patentability dated Oct. 14, 2014 received for PCT Application No. PCT/US2013/036331.

Meeks, S., et al., "Optically Guided Patient Positioning Techniques", Seminars in Radiation Oncology, Jul. 2005, pp. 192-201, vol. 15, Issue 3. doi:10.1016/j.semradonc.2005.01.004.

Wagner, T., et al., "Optical Tracking Technology in Stereotactic Radiation Therapy", Medical Dosimetry, Jan. 2007, pp. 111-120, vol. 32, No. 2. doi:10.1016/j.meddos.2007.01.008.

Soete, G., et al., "Initial Clinical Experience With Infrared-Reflecting Skin Markers in the Positioning of Patients Treated by Conformal Radiotherapy for Prostate Cancer", Int. J. Radiation Oncology Biol. Phys., Sep. 2001, pp. 694-698, vol. 52, No. 3.

Benedict, S., et al., "Stereotactic body radiation therapy: The report of AAPM Task Group 101," Medical Physics, Aug. 2010, pp. 4078-4101, vol. 37, Issue 8.

Keall, P., et al., "The management of respiratory motion in radiation oncology report of AAPM Task Group 76," Medical Physics, Jul. 2006, pp. 3874-3900, vol. 33.

Walter, C., et al., "Phantom and in-vivo measurements of dose exposure by image-guided radiotherapy (IGRT): MV portal images vs. kV portal images vs. cone-beam CT," Radiotherapy and Oncology, Nov. 2007, pp. 418-423, vol. 85.

Yin, F., et al., "Integration of Cone-Beam CT in Stereotactic Body Radiation Therapy," Technology in Cancer Research and Treatment, Apr. 2008, pp. 133-139, vol. 7, No. 2.

Kim, H., et al., "Development of an optical-based image guidance system: Technique detecting external markers behind a full facemask," Medical Physics, May 27, 2011, pp. 3006-3012, vol. 38, No. 06.

Bova, F., et al., "The University of Florida Frameless High-Precision Stereotactic Radiotherapy System," International Journal of Radiation Oncology Biology Physics, Feb. 26, 1997, pp. 875-882, vol. 38, No. 04.

Ryken, T., et al., "Initial Clinical Experience With Frameless Stereotactic Radiosurgery: Analysis of Accuracy and Feasibility," International Journal of Radiation Oncology Biology Physics, Jul. 2001, pp. 1152-1158. vol. 51, Issue 4.

Tome, W., et al., "A High-Precision System for Conformal Intracranial Radiotherapy," International Journal of Radiation Oncology Biology Physics, Dec. 7, 1999, pp. 1137-1143, vol. 47, No. 4.

Baroni, G., et al., "Implementation and application of real-time motion analysis based on passive markers," Medical & Biological Engineering & Computing, Nov. 1998, pp. 693-703, vol. 36.

Baroni, G., et al., "Real-time three-dimensional motion analysis for patient positioning verification," Radiotherapy & Oncology, Nov. 12, 1999, pp. 21-27, vol. 54.

Yan, H., "The correlation evaluation of a tumor tracking system using multiple external markers," Medical Physics, Oct. 16, 2006, pp. 4073-4084, vol. 33, No. 11.

Stroian, G., et al., "Elimination of ghost markers during dual sensor-based infrared tracking of multiple individual reflective markers, " Medical Physics, Jun. 22, 2004, pp. 2008-2019, vol. 31, Issue 07.

Yan, G., et al., "Ghost marker detection and elimination in marker-based optical tracking systems for real-time tracking in stereotactic body radiotherapy," Medical Physics, Oct. 1, 2014, pp. 1-11, vol. 41, No. 10.

International Preliminary Report on Patentability dated Oct. 14, 2014, received for PCT Application No. PCT/US2013/036340.

International Search Report & Written Opinion dated Aug. 1, 2013, received for PCT Application No. PCT/US2013/036340.

Qian, J., et al., "Dose Verification for respiratory-gated Volumetric modulated arc therapy (VMAT)," Aug. 7, 2011, pp. 4827-4838.

* cited by examiner

PREVENTION OF SETUP ERRORS IN RADIOTHERAPY

CROSS-REFERENCE TO RELATED APPLICATIONS

This application is based upon and claims priority to U.S. Provisional Patent Application Ser. No. 61/623,395, entitled "DEVELOPMENT AND EVALUATION OF AN AMBIGUITY-FREE TRACKING SYSTEM FOR EXPANDED USE IN RADIOTHERAPY", filed Apr. 12, 2012, the disclosure of which is hereby incorporated by reference in its entirety.

STATEMENT REGARDING FEDERALLY SPONSORED RESEARCH

None.

FIELD OF THE INVENTION

The present invention generally relates to the field of radiotherapy, and more particularly relates to optical tracking systems.

BACKGROUND OF THE INVENTION

Treatment of a wrong body part due to incorrect setup is among leading types of errors in radiotherapy. Safe delivery of a highly conformal dose distribution to a well-defined target volume in radiotherapy is becoming more complicated due to use of advanced treatment techniques such as intensity-modulated radiation therapy (IMRT) and volumetric-modulated arc therapy (VMAT). Radiotherapy is a complicated multi-step, multi-person process and errors can occur at any point. One cause for radiotherapy errors is geometric miss caused by incorrect patient setup. Geometric miss is typically defined as treatment of incorrect body parts with more than 10 mm spatial discrepancy. Geometric miss can result in significant under-dose to the target which can cause tumor recurrence, and over-dose to healthy tissue with severe normal-tissue complications. In hypo-fractionated radiotherapy such as stereotactic body radiotherapy (SBRT), it may result in even more severe morbidity than traditional radiotherapy.

A challenge in patient setup is to accurately localize a patient, in each treatment session, to a same planned treatment position. The past decade has seen rapid expansion in technological tools and processes to facilitate accurate patient localization. Examples include patient immobilization devices with couch indexing ability and image-guided radiotherapy (IGRT). Indexed patient immobilization devices not only ensure repeatable patient fixation, but also reduce patient setup errors by providing initial approximate target localization. X-ray based image-guided technologies, such as cone beam computed tomography (CBCT), enable the visualization of internal anatomy with sufficient soft tissue contrast. Such technologies allow corrections for misalignment or interfraction motion through registration with reference CT images. Non-radiographic image-guided technology systems such as AlignRT® (Vision RT Ltd., London, UK), SonArray® (Varian Medical Systems Inc., Palo Alto, Calif.), and ExacTrac® (BrainLab AG, Heimstetten, Germany) have also been developed for the purpose of patient setup guidance as well as continuous monitoring throughout treatment. These systems have the potential to eliminate patient setup errors and significantly reduce setup uncertainty.

However, employment of these advanced technological equipment and tools does not guarantee that radiotherapy is immune to setup errors. Patient setup is a process that cannot be automated, and, therefore, is subject to human errors. There are several contributing factors. First, sufficient formal training is not always provided to personnel who operate the devices and interpret the results. Incorrect interpretation leads to incorrect adjustment of treatment position, and, therefore setup errors. For example, a great risk in treating thoracic spine is the treatment of the wrong vertebral body. Due to similarities in bony structure in this region, incorrect alignment could occur as a result of misregistration using either orthogonal imaging or CBCT. Second, as complexity of tools increases, complexity of control over the tools and workload for therapists increases significantly as well, as evidenced by the increasing number of computer monitors, or displays, in a control room. Therapists could lose attention to correctness of treatment delivery when streamlined workflow and standardized control is lacking. Third, while most IGRT devices have great geometric precision, they have limitations which could disadvantageously impact their ability to ensure patient safety. For example, widely used radiographic systems, such as CBCT, do not track patient position change, and thus only represent the position of a patient at the time of image acquisition. After CBCT imaging, a treatment couch could be accidently moved for some reason (e.g., clearance check), and not moved back to an intended treatment position. In addition, CBCT cannot be performed for non-coplanar setups, meaning that imaging position would differ from treatment position. For this reason, therapists on machines equipped with multiple IGRT devices often find themselves switching between devices from one patient to another, depending on a treatment site of each patient. As another example, non-radiographic image-guided technology systems, such as ExacTrac® and AlignRT®, are usually not general-purpose systems and are only applicable to limited disease sites. Fourth, immediate and independent position verification is not always available to a therapist to show that the patient has been positioned exactly as planned, especially when the above-mentioned limitations of the employed IGRT systems are encountered.

Commercially available non-radiographic tracking systems such as ExacTrac®, frameless SonArray®, and AlignRT® have long been used for patient setup and monitoring, due to their high-precision and continuous tracking ability. However, they all have limitations compared to the method and apparatus in accordance with the invention when trying to use them on a large scale as on a general-purpose patient setup system. Designed to monitor patient motion (both translation and rotation) during treatment, ExacTrac® requires at least four (4) infra-red reflective markers to be affixed on a patient in each treatment session, which not only introduces significant workload to a therapist but also may act as a source of error. The frameless SonArray® system, which connects infra-red reflective markers in a fixed pattern to a patient through a bite block, is only employed in the treatment of brain targets. Similarly, 3D surface imaging-based AlignRT® is not for general-purpose use, and is predominantly used only in the treatment of brain, head and neck, or breast patients. Most importantly, each of these known systems lacks a streamlined workflow which may discourage their large-scale use in a busy clinic.

One known method uses one fiducial marker to improve spine image registration robustness. In such known method, a nearly correct transformation can be obtained by aligning the fiducial marker, which significantly improves registration successful rate. However, this known method disadvantageously requires a surgical implantation procedure.

SUMMARY OF THE INVENTION

In one embodiment, a method, with a computer, of tracking changes in position of a patient while the patient is undergoing radiotherapy is disclosed. The method comprises placing a computed tomography ball bearing at a location on a surface of one of a face mask and an immobilization device for a patient; performing a treatment-simulation computed tomography scan of the patient; calculating, with the computer, coordinates of the computed tomography ball bearing, based on the treatment-simulation computed tomography scan of the patient; removing the computed tomography ball bearing from the surface of the one of the face mask and the immobilization device; placing an infra-red reflecting marker at the location of the one of the face mask and the immobilization device; storing, in a database communicatively coupled to the computer, the coordinates of the computed tomography ball bearing as predicted coordinates of a predicted location of the infra-red reflecting marker. The method also comprises, while the patient is receiving radiotherapy with a linear accelerator: determining a real-time location of the infra-red reflecting marker; comparing, with the computer, the real-time location of the infra-red reflecting marker with the predicted location of the infra-red reflecting marker; and displaying results of the comparing in a graphical user interface of a display communicatively coupled to the computer.

In second embodiment, a method, with a computer, of tracking changes in position of a patient while the patient is undergoing radiotherapy is disclosed. The method comprises placing a computed tomography ball bearing at a location on a surface of the patient; performing a treatment-simulation computed tomography scan of the patient; calculating, with the computer, coordinates of the computed tomography ball bearing, based on the treatment-simulation computed tomography scan of the patient; removing the computed tomography ball bearing from the surface of the patient; making a tattoo on skin of the patient at the location of the computed tomography ball bearing; placing an infra-red reflecting marker at the location of the tattoo; storing, in a database communicatively coupled to the computer, the coordinates of the computed tomography ball bearing as predicted coordinates of a predicted location of the infra-red reflecting marker. The method also comprises, while the patient is receiving a first session of radiotherapy with a linear accelerator: determining a real-time location of the infra-red reflecting marker; comparing, with the computer, the real-time location of the infra-red reflecting marker with the predicted location of the infra-red reflecting marker; and displaying results of the comparing in a graphical user interface of a display communicatively coupled to the computer.

The second method may include, in an embodiment, the steps of: removing the infra-red reflecting marker from the location of the tattoo on the skin of the patient after completion of the first session of radiotherapy; maintaining the tattoo on the skin of the patient until occurrence of at least one additional session of radiotherapy subsequent to the first session of radiotherapy; and placing an infra-red reflecting marker at the location of the tattoo prior to start of the at least one additional session of radiotherapy.

The second method may also include, in an embodiment, the step of retrieving, with the computer, from the database the coordinates of the computed tomography ball bearing as the predicted coordinates of the predicted location of the infra-red reflecting marker.

The second method may further include, in an embodiment, while the patient is receiving the at least one additional session of radiotherapy with the linear accelerator: determining the real-time location of the infra-red reflecting marker, comparing, with the computer, the real-time location of the infra-red reflecting marker with the predicted location of the infra-red reflecting marker, and displaying results of the comparing in the graphical user interface of the display.

BRIEF DESCRIPTION OF THE DRAWINGS

The accompanying Figures, in which like reference numerals refer to identical or functionally similar elements throughout the separate views and which together with the detailed description below are incorporated in and form part of the specification, serve to further illustrate various embodiments and to explain various principles and advantages all in accordance with the present invention, in which.

DETAILED DESCRIPTION

As required, detailed embodiments of the present invention are disclosed herein. However, it is to be understood that the disclosed embodiments are merely examples of the invention, which can be embodied in various forms. Therefore, specific structural and functional details disclosed herein are not to be interpreted as limiting, but merely as a basis for the claims and as a representative basis for teaching one skilled in the art to variously employ the present invention in any appropriately detailed structure and function. Furthermore, the terms and phrases used herein are not intended to be limiting; but rather, to provide an understandable description of the invention.

Figure 1:
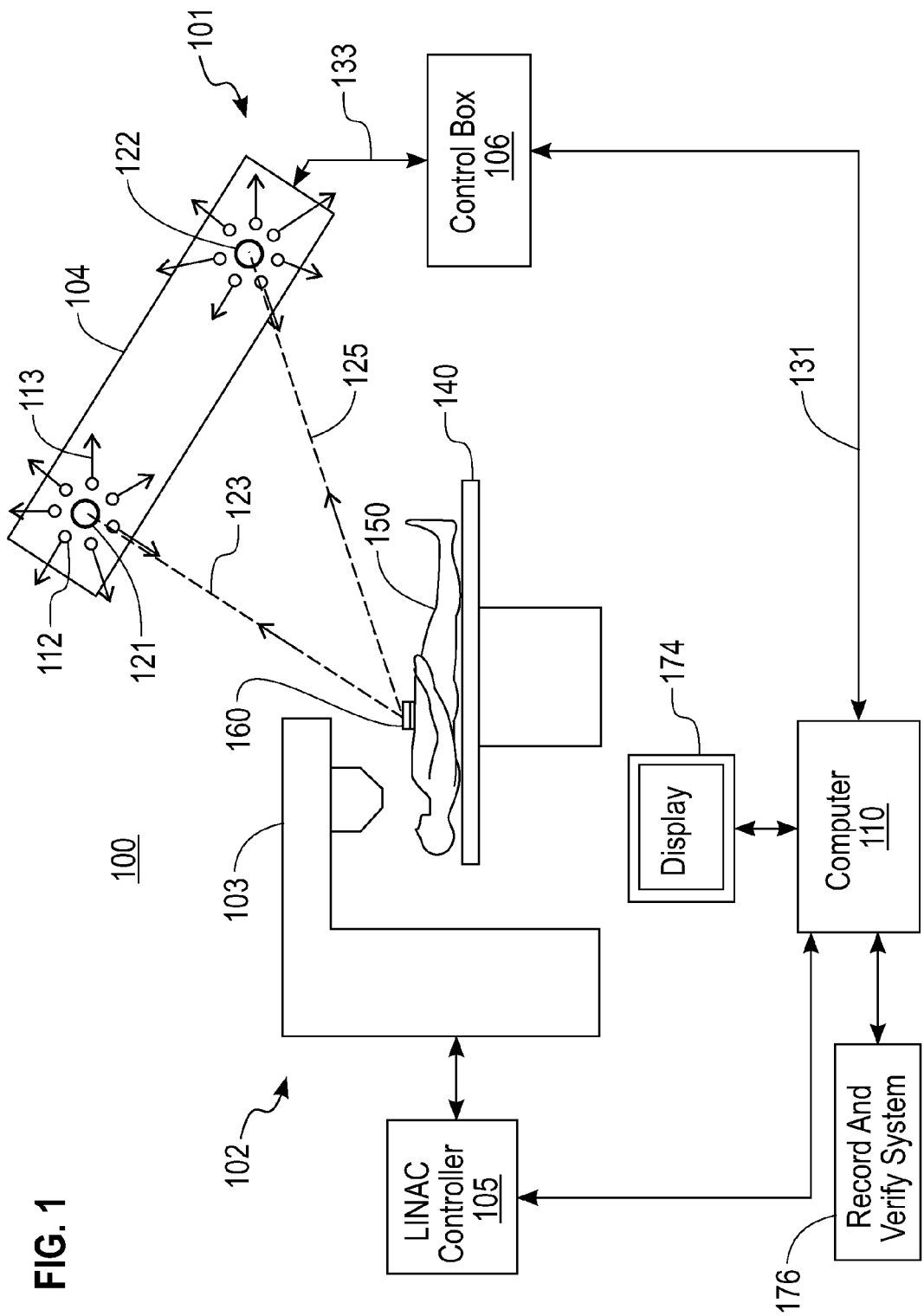
FIG. 1 is a simplified block diagram of an optical tracking system in accordance with one embodiment of the invention, and a radiation delivery system.

FIG. 1 is a simplified block diagram of a patient safety system 100 in accordance with the invention. The patient safety system (hereinafter "PSS") 100 uses optical tracking technology to prevent gross patient setup errors (hereinafter "setup errors"). The PSS 100 comprises an optical tracking system 101 in accordance with the invention, and a radiation delivery system 102. The radiation delivery system 102 is a conventional system except as noted hereinbelow. In one embodiment, the radiation delivery system 102 includes a dual energy linear accelerator (hereinafter "LINAC") 103 for performing external beam radiotherapy and a controller 105 for controlling the LINAC.

The optical tracking system 101 comprises a position sensor unit 104, a control box 106, a computer 110, such as a personal computer, and software. The position sensor unit 104 is mounted on a ceiling of the treatment room. The position sensor unit 104 includes one or more illuminators 112 for emitting infrared (IR) light as indicated by arrows 113, and two charge-coupled device cameras (hereinafter "cameras") 121 and 122 for receiving reflected IR light as indicated by dotted lines 123 and 125. In one embodiment, the optical tracking system 101 uses a Polaris® position sensor unit by Northern Digital, Inc., of Waterloo, Ontario. In one embodiment, the computer 110 is located in a LINAC treatment room (hereinafter "treatment room"). Software residing in the computer 110 communicates with the control box 106. The software comprises computer program instructions, or code, for executing the methods described herein, and for communicating with the control box 106. The computer 110 is connected to the control box 106 through a serial cable 131. The control box 106 is connected to the position sensor unit 104 through a proprietary cable 133.

The radiation delivery system 102 includes a treatment couch (hereinafter "couch") 140. A patient 150, who is undergoing radiation treatment, or radiotherapy, is shown lying on the couch 140. With the PSS 100, a specially-designed infra-red reflective marker (IRRM) 160 is affixed on a surface of the patient 150. The position sensor unit 104 is mounted above a foot of the couch 140. In one embodiment, the two cameras 121 and 122 of the position sensor unit 104 are 50 cm apart. Real-time position of the IRRM 160 is captured approximately fifteen (15) frames per second, i.e., 15 Hz, by the cameras 121 and 122. An internal processing unit (not shown) of the position sensor unit 104 performs triangulation, based on IR light reflections from the IRRM 160 and received by the cameras 121 and 122 which act as sensors. The position sensor unit 104 determines three-dimensional (3D) coordinates of the IRRM 160 in a native coordinate system of the optical tracking system 101, and sends the 3D coordinates to the computer 110. The control box 106 of the optical tracking system 101 works in passive mode, i.e., it responds to each command (e.g., initialize the cameras 121 and 122; read location of the IRRM 160; close the connection, etc.) sent from the computer 110 but the control box does not initiate any communication. Inquiries and requests from the computer 110 are sent to the control box 106, and the control box responds with coordinates of the IRRM 160 in a camera native coordinate system. A calibration procedure, described hereinbelow, is designed to transform the coordinate system from the camera native coordinate system to a coordinate system of the LINAC 103.

The computer 110 is communicatively coupled to a display 174 that presents, via a graphical user interface (see FIG. 4), information about the PSS 100 to an operator such as a CT therapist (hereinafter "therapist"). The computer 110 is communicatively coupled to a record and verify (R&V) system 176, such as the MOSAIQ® R&V system by Elekta, Inc., of Sunnyvale, Calif. The PSS 100 achieves a seamless clinic workflow by synchronizing with the R&V system 176. By semi-permanently mounting the single IRRM 160 on a patient's skin or on an immobilization device (hereinafter "immobilization device"), therapist intervention is eliminated or minimized. Overall results showed that the PSS 100 has sufficient accuracy to catch gross setup errors greater than 1 cm in real-time. The PSS 100 prevents gross setup errors in radiotherapy. The PSS 100 can be applied to all treatment sites for independent positioning verification. The PSS 100 complements complex image-guidance systems due to the PSS's advantages of continuous tracking ability, due to a lack of any radiation dose from the PSS, and due to the PSS allowing a fully automated clinic workflow.

Figure 2:
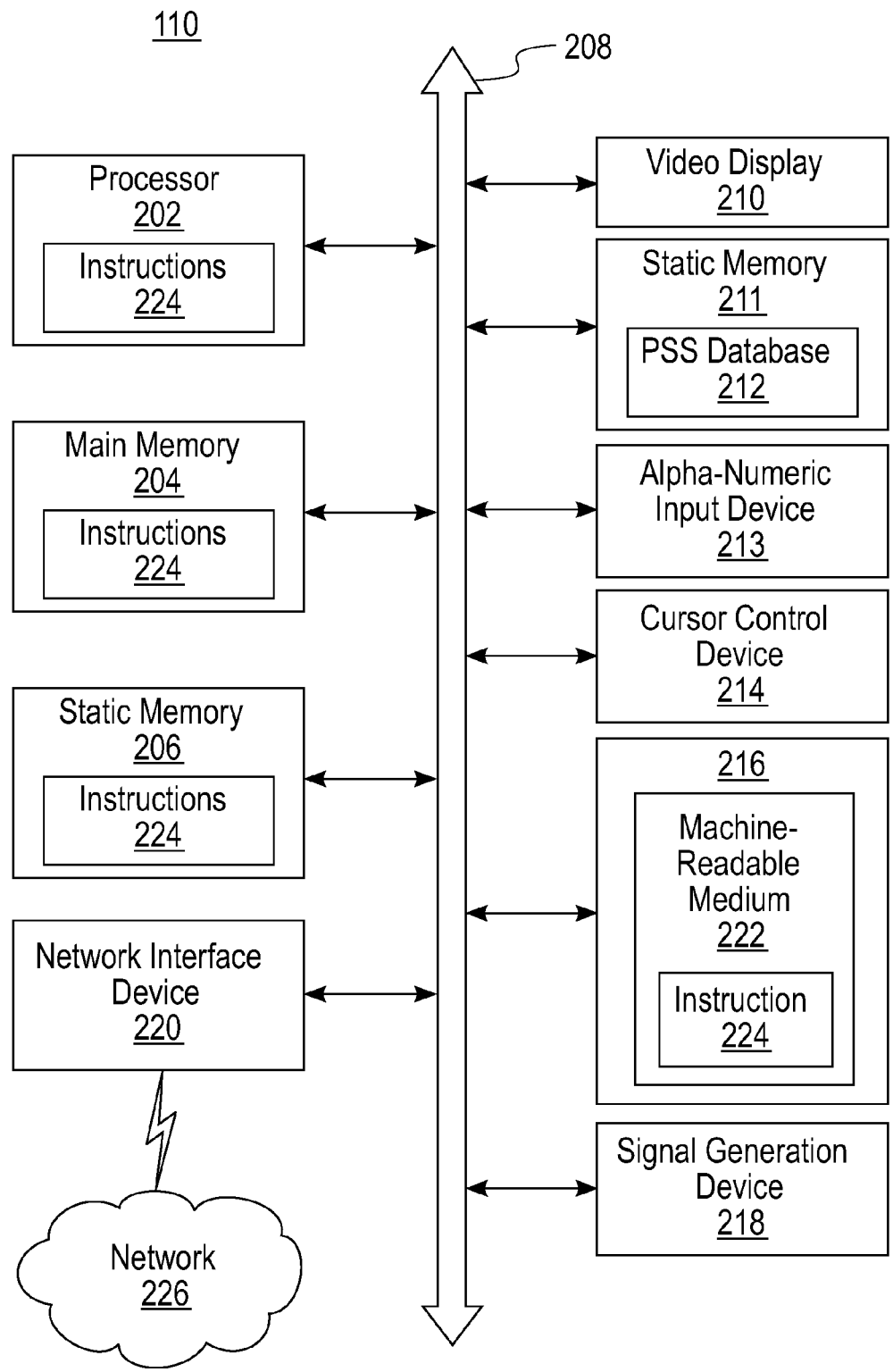
FIG. 2 is a simplified block diagram of one embodiment of the computer shown in FIG. 1.

FIG. 2 is a simplified block diagram of the computer 110. The computer 110 may include a processor 202 (e.g., a central processing unit (CPU), a graphics processing unit (GPU) or both); a main memory 204 such as random access memory (RAM); and a static memory 206, such as read-only memory (ROM) or a hard disk, that holds instructions, which communicate with each other via a bus 208. The bus 208 is connected to a display controller 210 which is coupled to the display 174 such as a liquid crystal display (LCD). The display 174 is used to show, or present, information about the computer 110. The computer 110 may also include another static memory 211, such as a hard disk, that holds a PSS database (DB) 212; an input device 213 such as a keyboard; a cursor control device 214 such as a mouse or a trackpad; a memory device 216 such as disk drive unit or solid state memory, a signal generation device 218 such as a speaker or audible alarm; and a network interface device 220, which are coupled to the bus 208. The disk drive unit 216 may include a tangible computer-readable storage medium 222 on which is stored one or more sets of instructions 224 (i.e., software) embodying any one or more of the methods or functions described herein, including those methods illustrated herein. The instructions 224 may also reside, completely or at least partially, within the main memory 204, the static memory 206, and/or within the processor 202 during execution thereof by the computer 110. A set of instructions 224, when executed, may cause the computer 110 to perform any one or more of the methods discussed herein. The main memory 204 and the processor 202 also may constitute non-transitory tangible computer-readable storage media. Although only one CPU 202 is illustrated for computer 110, a computer with multiple CPUs can be used equally effectively. Embodiments of the present invention also incorporate interfaces that each includes separate, fully programmed microprocessors that are used to off-load processing from the CPU 202. An operating system (not shown) included in the main memory is a suitable multitasking operating system such as any of the Linux, UNIX, Windows, and Windows Server based operating systems. Embodiments of the present invention are able to use any other suitable operating system. Some embodiments of the present invention utilize architectures, such as an object oriented framework mechanism, that allows instructions of the components of operating system (not shown) to be executed on any processor located within the information processing system. The bus 208 is also connected to a communication controller that conforms to, for example, an Ethernet protocol. The communication controller may be used to physically connect the computer 110 with a network. The network adapter hardware 220 is used to provide an interface to a network 226 as illustrated. Embodiments of the present invention are able to be adapted to work with any data communications connections including present day analog and/or digital techniques or via a future networking mechanism. Although the tangible computer-readable storage medium 222 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the computer and that cause the computer to perform any one of the methods discussed herein.

Patients undergo a treatment-simulation, computed tomography (CT) scan with a CT ball bearing (BB) placed over their surface close to an intended treatment site. Coordinates of the CT BB relative to an isocenter of the treatment room are used as reference for tracking. The CT BB is replaced with an IRRM 160 before treatment starts. In one embodiment, only a single CT BB is replaced by an IRRM 160. In other embodiments (not shown), each of more than one CT BB is replaced by an IRRM 160. The PSS 100 evaluates setup accuracy by comparing real-time position of the single IRRM 160 with a reference position. To automate workflow, the PSS 100 synchronizes with the R&V system 176 in real time and automatically loads in reference data for the patient 150 under treatment. Special IRRMs 160, which remain stuck to an aquaplastic face mask (hereinafter "face mask") or to a body mold throughout the course of treatment, minimize workload of the therapist. Accuracy of the PSS 100 was examined on an anthropomorphic phantom with a designed end-to-end test. Performance of the PSS 100 was also evaluated on head and neck (H&N) patients as well as abdominalpelvic patients using CBCT as a standard.

The PSS 100 addresses issues contributing to errors in patient setup and safeguards patient treatment. The PSS 100 utilizes the cameras to track the single IRRM 160 affixed on the patient's skin or on the immobilization device. Advantageously, the PSS 100 is applicable for all disease sites. The PSS 100 provides continuous and independent verification to therapists regarding patient setup accuracy. With a fully automated workflow, the PSS 100 complements complicated IGRT systems to ensure patient safety in radiotherapy.

To expand the use of an optical tracking system, the single IRRM 160 is used for patient localization, which is not possible with commercial systems. In a conventional setup, a patient is first positioned with a coarse laser-marker-based system. Then, the couch is manually shifted based on the distance between treatment isocenter and CT isocenter, calculated by a treatment planning system (TPS) such as the Pinnacle TPS by Philips Radiation Oncology Systems of Fitchburg, Wis. Portal images are usually acquired to register with digital reconstructed radiograph for fine tuning and verification. If CBCT is used for positioning, CBCT images are registered with reference CT. Errors may be introduced in the registration process when treating areas in close proximity to spine or extremities. In such area, intensity-based image registration is susceptible to being trapped at one of possibly several local optima. On the other hand, with the use of the optical tracking system and just a single IRRM 160, the PSS 100 effectively prevents such errors. With the PSS 100, a position of the single IRRM 160 in the treatment room, and therefore patient localization, can be accurately predicted by the TPS. Prepositioning, based on the coordinates that the PSS 100 obtains from IR light reflections from the single IRRM 160, can place the patient 150 closer to a correct treatment position and minimize a possibility of the registration being trapped at a local optimum. The PSS 100 advantageously uses only a single IRRM 160 for conventional radiotherapy treatment when no non-coplanar beams are involved. More IRRMs 160 could be used for improved accuracy, but the increase in workload is minimal when a single IRRM 160 is used, and it is sufficient to use a single IRRM 160 when a relatively large target margin is used and no non-coplanar treatments are involved. The PSS 100 is a one-marker, noninvasive solution, independent of couch or gantry, and the PSS facilitates successful image registration and effectively avoids treating wrong patient sites. When daily imaging is not employed to position the patient 150, treatment position can be reproduced quickly by the optical guidance system with reasonable accuracy. This strategy may be most attractive to conventional radiotherapy where a considerable margin is assigned to account for target displacement.

Figure 3:
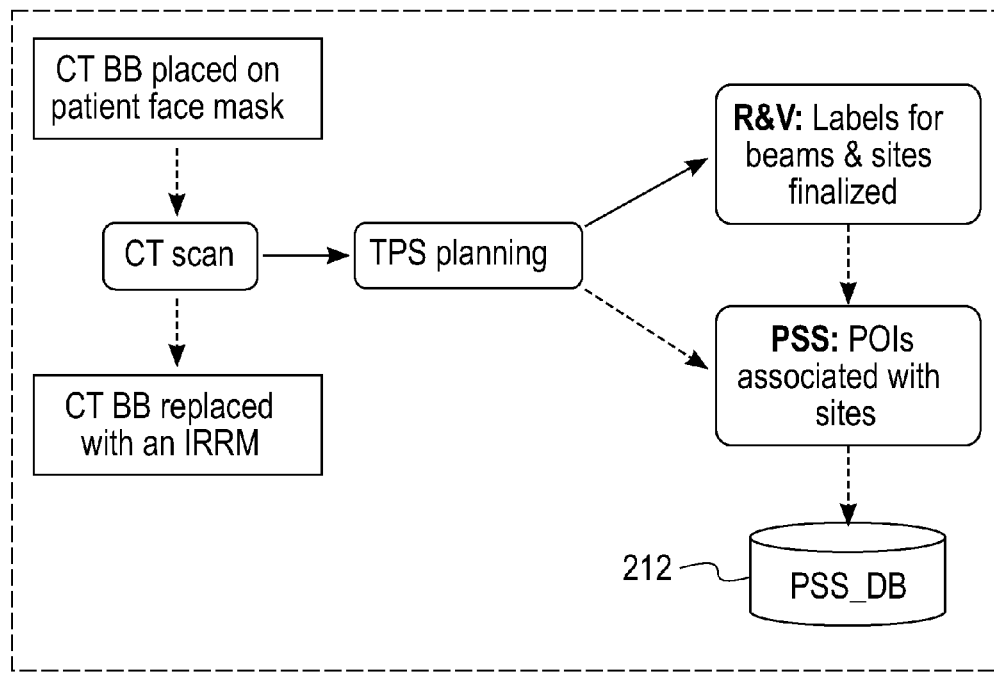
FIGS. 3 and 4 are flow diagrams of one embodiment of a method of a patient safety system used with the optical tracking system and the radiation delivery system shown in FIG. 1.
Figure 4:
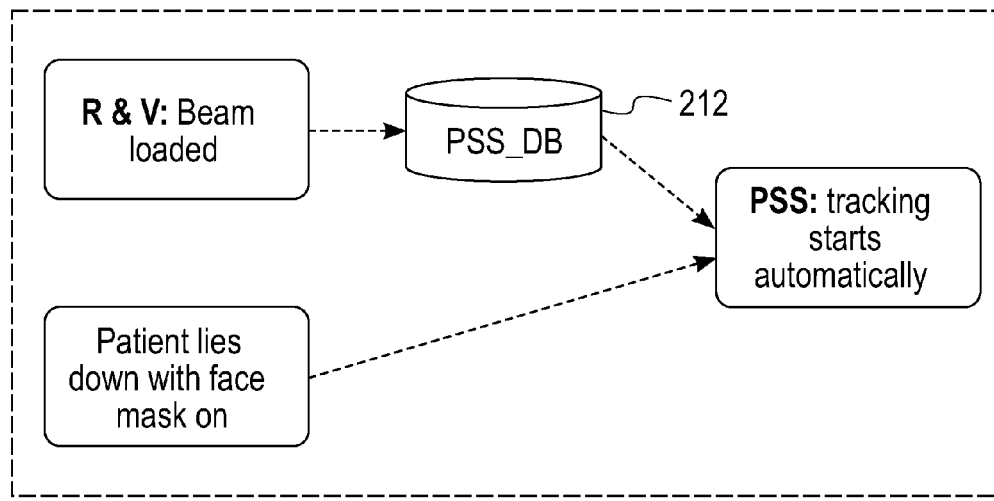

FIGS. 3 and 4 are flow diagrams of one embodiment of a method of the PSS 100 used with the optical tracking system 101 and the radiation delivery system 102. With the PSS 100, workload added to a therapist is minimal and smooth clinical workflow is maintained. Minimal workload also helps reduce the possibilities of human errors. FIGS. 3 and 4 show a demonstrative workflow of the PSS 100 when used on a H&N patient treated with a face mask. FIG. 3 relates to a preparation stage. In the preparation stage, reference tracking information is created by associating POIs exported from the TPS with treatment beams and sites exported from the R&V system 176. Arrows represent work or data flow introduced by the PSS 100. FIG. 4 relates to a treatment stage. In the treatment stage, reference tracking information retrieval is triggered by beam loading in the R&V system 176. Arrows represent data flow introduced by the PSS 100 and completed without user intervention.

A feature of the PSS 100 is its automatic workflow, which is essential in a busy clinical environment. Workflow automation not only improves efficiency but also minimizes chances of human errors. Workflow automation is achieved in two steps: 1) mounting an IRRM 160 permanently on a patient immobilization device (placing the IRRM 160 on the patient's skin requires mounting and unmounting of the IRRM 160 during each treatment session); and 2) automatic patient information loading by communicating with the R&V system 176. The PSS 100 includes information exchange between the PSS, the R&V system 176 and the TPS.

While a dosimetrist is preparing a treatment plan based on the patient's CT datasets, or image sets, the dosimetrist identifies the BB and defines one treatment isocenter for each site as POI with x y z coordinates in the TPS. When the treatment plan has been prepared, both POIs (one POI for the CT BB, and one POI for the isocenter) are sent directly to the database 212 of the PSS 100. At a same time, the dosimetrist sends the treatment plan data, including treatment beam IDs and site names, to the R&V system 176. This information, after finalized and approved in the R&V system 176, is exported to the database 212 of the PSS 100, to be associated with POIs exported from the TPS. After these two steps, a patient entry in the database 212 of the PSS 100 includes a patient medical record number (MRN), patient POIs, patient treatment beam IDs, treatment site(s), and association between treatment site(s) and POIs. A patient 150 can have multiple treatment sites and each site can have different treatment isocenters.

The R&V system 176 is configured such that when a treatment beam is loaded it outputs a binary file to a pre-specified network location. The binary file includes a currently-loaded patient MRN, a treatment beam ID, and treatment site(s). The PSS 100 searches this location every three (3) seconds for such a binary file. Once such a binary file is found, the PSS 100 uses information contained in the binary file to search the database 212 and retrieve POIs for currently loaded treatment beam and site. The only information that the PSS 100 needs for tracking is the POI coordinates for treatment isocenter and the POI coordinates for the BB. This step is fully automated and no user intervention is needed.

Prior to the PSS 100 being used, the coordinate system of the optical tracking system is converted from its native coordinate system to a coordinate system of the treatment room. A calibration procedure converts the native coordinate system of the optical tracking system to an absolute treatment room coordinate system. A calibration jig comprising five (5) commercial IRRMs (not shown) is used for the calibration procedure. The coordinates of each commercial IRRM relative to a center of the calibration jig is determined via CT scan and collected in a 5×3 matrix A. The calibration jig is then placed on a couch with a center of the calibration jig aligned with an isocenter of the machine under the guidance of CBCT. The coordinates of the commercial IRRMs are sampled by the cameras and collected into another matrix B. A rotation matrix R and a translation matrix T satisfying $$A = BR + T$$

is solved by minimizing the following expression $$\epsilon^2 = \|A - BR - T\|.$$

This is known as the relative pose problem in computer vision. A general analytical solution via singular value decomposition (SVD) is employed, and steps thereof are summarized as following. 1) The centroids $<A_c>$ and $<B_c>$ are subtracted from A and B, respectively, to align the origins of the two coordinate systems. 2) The SVD of $B^T A$ is computed as $$B^T A = UWV^T,$$

where U and V are unitary matrices and W is a diagonal matrix whose diagonal entries equal to the singular values of $B^T A$. 3) The solutions of R and T are given as $$R = U \begin{pmatrix} 1 & 0 & 0 \\ 0 & 1 & 0 \\ 0 & 0 & \det(UV^T) \end{pmatrix} V^T,$$

and $$T = A_c - B_c R.$$

Patient preparation includes performing a treatment-simulation CT scan (hereinafter "CT simulation") on the patient, and transferring information obtained thereby from the TPS to the PSS 100. Prior to CT simulation, a CT BB is placed on the patient's surface at a location close to an intended treatment area to ensure that the CT BB is included in the scan. After the CT simulation is performed, the CT BB is removed and its location is marked with a skin tattoo. The CT BB is identified as a point of interest (POI) in the TPS. Then, coordinates of the POI and coordinates of each treatment isocenter are sent to a designated network folder. An approved treatment plan in the TPS is transferred to the R&V system 176 where treatment beams and treatment sites are appropriately labeled and finalized before physics approval. The approved treatment plan (including treatment beams and their associated sites) is then exported from the R&V system 176 in a radiation treatment plan (RTP) format to a same network folder. A data import module of the PSS 100 associates each treatment site in a RTP file with POIs exported from the TPS, including treatment isocenter and the CT BB. The CT BB is replaced with an IRRM 160 at time of treatment. The coordinates of the CT BB relative to a respective treatment isocenter of each treatment site predict the coordinates of the IRRM 160 at time of treatment. All treatment beams and their associated treatment sites in the RTP file are imported into the database 212 of the PSS 100 to facilitate workflow automation in the treatment stage, as described below.

In one embodiment, external beam radiotherapy is performed on a Synergy® LINAC by Elekta Oncology Systems Ltd., of Crawley, UK. The R&V system 176 for the LINAC is configured to create an external file when a treatment beam is loaded. The external file contains patient identification and a label of a currently loaded treatment beam. The PSS 100 uses the label of the currently loaded treatment beam to retrieve the associated treatment site, and, in turn, reference tracking data from the database 212 of the PSS for the patient 150. With the PSS 100, patient information loading is thus fully automated and no therapist intervention is necessary. When setting up the patient 150 for treatment, a therapist locates a skin tattoo indicating a position of the CT BB and places a specially-designed, disposable, flat-surfaced IRRM 160 at a location of the skin tattoo. The IRRM 160 is fabricated by covering one side of a piece of round double-sided sticky tape (6 mm diameter and 1 mm height) with reflective tape. The other side is protected by a peelable sheet which makes mounting of the IRRM 160 easy. The PSS 100 uses the IRRM 160 as surrogate to verify patient setup. Any discrepancy (in three dimensions) between a treatment room position and a reference position of the IRRM 160 is continuously monitored and presented on the display 174 located in the treatment room. A same information is presented on another display located in the control room. If the discrepancy exceeds pre-specified thresholds, the therapist can take appropriate corrective action with assistance of a physicist. To cope with non-coplanar treatment, a vector connecting the isocenter of the treatment room and the CT BB is rotated around a vertical axis in the same way (direction and angle) as the couch rotates to predict treatment room coordinates of the IRRM 160.

With the above-described workflow, at each treatment session, the therapist locates the skin tattoo and places the IRRM 160. To repeat this for each patient could be a significant burden to the therapist, and a potential source of error because the IRRM 160 could be placed at a wrong location. Likelihood of such errors increases if the patient had already gone through multiple radiotherapy courses, which could leave multiple skin tattoos on the patient.

To minimize workload and avoid potential errors, a location of the IRRM 160 can be permanently transferred from the patient's skin to a spot on the immobilization device. This is easy to achieve for a patient treated with a face mask (for brain or H&N disease). The CT BB is directly affixed on the face mask at time of the CT scan and replaced with an IRRM 160 afterward. A location of the CT BB is selected to be over the patient's chin area which can ensure visibility of the CT BB to both cameras in the treatment room. With this approach, the IRRM 160 is readily available before treatment starts. Workflow of the PSS 100 is fully automated and no intervention is needed from the therapist in the treatment room. Once a beam (typically setup beam) is loaded into the R&V system 176 and the face mask is placed on the patient 150, the PSS 100 automatically starts to track the IRRM 160 continuously and evaluate setup accuracy.

A same approach can be applied for patients treated with a body mold (for patients with disease not in the brain or H&N area). For patients with disease in their extremities, a location on the body mold close to the disease can be conveniently selected to place the CT BB. For patients with disease in abdominalpelvic area, placement of the CT BB can be problematic. At a time of CT simulation, it may be difficult to locate a spot on the body mold that simultaneously guarantees 1) the visibility of the CT BB in CT images 2) the visibility of the IRRM 160 (replacing the CT BB after the scan) to both cameras, and 3) that the IRRM 160 will not be easily scraped off when the patient 150 gets in and out of the body mold for treatment. For these reasons, an alternative workflow is adopted in these cases. The CT BB is placed on the patient's skin during CT scan and marked with a skin tattoo afterward. In a first treatment session, the therapist locates the tattoo and temporarily places an IRRM 160 for initial verification. The IRRM 160 can be installed on a small plastic plate for easy handling. Once the verification is successful, a convenient location on the body mold is selected to permanently mount the IRRM 160. Without concern of CT scan range, it is relatively easy to pick an ideal spot on the body mold. The selected convenient location ensures visibility of the IRRM 160 to the cameras and the selected convenient location is such that the patient 150 cannot easily scrape off the IRRM 160. The selected convenient location of the IRRM 160 is then captured as reference for future treatment sessions. No therapist intervention is needed after the first treatment session.

To use the PSS 100, a total time in patient preparation is less than 5 minutes. For brain, H&N and extremity patients, the CT BB is placed on immobilization devices and replaced with an IRRM 160 after CT scan, and no skin tattoo is needed.

Accuracy of IRRM 160 placement, including patients with disease in extremities, is typically within 1-2 mm. A location on the body mold, next to intended treatment area, can be selected for CT BB placement. Preparation for a patient with disease in abdominalpelvic area requires a CT BB to be placed on the patient in the scan, and a skin tattoo to indicate its location.

For abdominalpelvic patients, the CT BB is affixed on the patient's skin, thus requiring a skin tattoo. In one method in accordance with the invention, two sets of skin tattoos are made for each abdominalpelvic patient to assist patient setup (mainly body rotation correction). Each set includes one anterior and two side tattoos, with one on each side of the patient 150. Either of the two anterior tattoos, when included in CT scan, can be selected to affix the CT BB. Therefore, to use the PSS 100, an extra tattoo does not need to be made.

An inferior anterior tattoo, which is easier to access when the patient 150 lies on the couch, can be used with the PSS 100 if the inferior anterior tattoo is included in the scan. Otherwise, a superior anterior tattoo can be used. Patient preparation for the PSS 100 adds less than 2 minutes to total CT simulation time.

Information transfer from the TPS to the PSS 100, implemented with a scripting language and standard FTP (file transfer protocol), is accomplished with a single button click in the TPS. An efficient software module is implemented to combine information from the TPS and the R&V system 176 and to import such combined information into the database 212 of the PSS 100.

In the treatment stage, if an IRRM 160 has been mounted on an immobilization device, no therapist intervention is needed. Otherwise, a therapist locates a selected anterior skin tattoo for initial verification, selects a location on immobilization device to permanently mount an IRRM 160, and captures the new location with the PSS 100. This procedure adds approximately two to three minutes to patient setup time in the first treatment session.

The PSS 100 constantly monitors currently loaded treatment beam and uses this information to automatically retrieve reference tracking information. If an IRRM 160 is already attached to patient immobilization devices (face mask or body mold), the PSS 100 starts tracking immediately. Otherwise, the therapist temporarily places an IRRM 160 plate over the intended skin tattoo for initial verification. If passed, a convenient location on the body mold (e.g., next to the patient's arm or knee) is selected to permanently mount the IRRM 160. A location of the IRRM 160 is captured by the cameras as new reference. In the former case, no therapist intervention is needed at all to use the system; in the latter case, the extra workload adds 2-3 minutes to patient setup time, but only in the first treatment session. No intervention is needed in future treatment sessions.

A daily quality assurance (QA) procedure is used to ensure the accuracy and consistency of the PSS 100. The PSS 100 uses a simple and efficient daily QA procedure that can be integrated with other daily QA activities, the majority of which are performed with a daily QA device such as the Daily QA3® device by Sun Nuclear Corp., of Melbourne, Fla. At time of initial calibration of the PSS 100, an IRRM 160 is permanently mounted on an end side of the daily QA device, facing the cameras. After aligning the daily QA device to the isocenter of the treatment room with a CBCT system (such as the XVI CBCT system by Elekta, Inc., of Sunnyvale, Calif.), a reference position of the IRRM 160 is captured and is associated with a daily QA beam in the R&V system 176. As a result of daily IGRT QA, the daily QA device is aligned to the isocenter of the treatment room with CB CT guidance. When the daily QA beam is loaded in the R&V system 176, consistency of the PSS 100, which is indicated by position variation of the IRRM 160, is immediately presented on the display.

Short term stability of the PSS 100 is evaluated by monitoring the IRRM 160 mounted on the daily QA device for a 10-minute period. The cameras are sufficiently warmed prior to conducting a short term stability study and the daily QA device is kept stationary on the couch during the short term stability study. Real time position of the IRRM 160 is captured with the cameras of the sensor unit, and the real-time position of the IRRM 160 is recorded in a log file for analysis. Variations of IRRM 160 position during the 10-minute period in each orthogonal direction are used to evaluate the short term stability of the PSS 100. Long term stability of the PSS 100 is also evaluated with the daily QA device, using a same setup for daily QA. The daily QA device is aligned to the isocenter of the treatment room with CBCT guidance once a week over a 12-week period. Long term stability of the PSS 100 was assessed with position variations of the IRRM 160 in these tests. Results of a short term stability test are shown in Table 1.

TABLE 1

|  |  | $\Delta$LAT (mm) | $\Delta$LNG (mm) | $\Delta$AP (mm) | $\Delta$VECT (mm) |
| --- | --- | --- | --- | --- | --- |
| (A) N = 9000 | SD | ±0.0 | ±0.1 | ±0.1 | ±0.1 |
|  | max (abs.) | 0.2 | 0.3 | 0.2 | 0.4 |
| (B) N = 12 | mean ± SD | 0.5 ± 0.4 | 0.5 ± 0.5 | 0.6 ± 0.5 | 1.0 ± 0.6 |
|  | max (abs.) | 1.3 | 1.6 | 1.5 | 2.0 |

Abbreviations:
LAT: lateral dimension;
LNG: longitudinal dimension;
AP: anteroposterior direction;
VECT: 3D Vector;
SD: standard deviation Shown in portion (A) of Table 1: short term stability as evaluated by observing position variation of a stationary IRRM 160 during a 10-minute span (9000 samples). Shown in portion (B) of Table 1: long term stability during a 12 week span as evaluated by observing weekly position variation of the IRRM 160 mounted on a daily QA device. The IRRM 160 was positioned to a same location under CBCT guidance. A standard deviation of variation in position during the 10-minute period was close to zero in all directions. Maximum variation was 0.3 mm along the longitudinal direction. This variation was due, in part, to vibrations in the ceiling. Portion (B) of Table 1 shows results of a long term stability test, in which the IRRM 160 was positioned to a same location weekly along with the daily QA device under CBCT guidance. An evenly distributed deviation was observed along the three axes with mean errors of 0.5±0.4 mm, 0.5±0.5 mm and 0.6±0 5 mm for lateral, longitudinal and anteroposterior direction, respectively. The combined 3D deviation was 1.0±0 6 mm on average, with a maximum of 2.0 mm. The deviation included uncertainty from CBCT image registration as well as automatic couch movement. The accuracy of both the CBCT image registration and automatic couch movement was about 1.0 mm.

Accuracy of the PSS 100 was evaluated with an anthropomorphic head phantom in an end-to-end test. A head phantom was scanned on a multi-slice CT scanner such as the Brilliance™ multi-slice CT scanner by Philips Medical Systems of Cleveland, Ohio To investigate an effect of different CT BB locations, five CT BBs were affixed on the phantom for CT scan. One CT BB was located directly over the chin area and the other four were at random locations on the phantom surface. All CT BBs were replaced with IRRMs 160 after the scan. A head phantom isocenter was arbitrarily defined inside the head phantom in the TPS. Coordinates of the head phantom isocenter and coordinates of the CT BBs were then sent to the PSS 100. In the treatment room, the head phantom was positioned to a treatment isocenter under guidance of CBCT. The PSS 100 uses one IRRM 160 at a time, with the other four IRRMs 160 blocked from the camera, to verify setup accuracy.

To evaluate an ability of the PSS 100 to detect large movement of the couch, the phantom was positioned to 12 different locations by shifting the couch ±5 cm or ±10 cm along each axis. The PSS-observed shifts of the couch were compared to nominal shifts of the couch. The IRRM 160 over the chin area was used in this study. Its room coordinates before shifts of the couch were captured as baseline. The above procedure was repeated with a 60° couch rotation to evaluate performance of the PSS 100 under non-coplanar treatment conditions. The results of a phantom study are shown in Table 2.

IRRMs 160, in portion (B): the test with couch shifts along each axis by 5 cm or 10 cm, and in portion (C): the same test as in (B) except with a 60° couch rotation. In the end-to-end test with five (5) individual IRRMs 160, mean error on all three axes was within 1.5 mm; the maximum deviation was 2.3 mm for both longitudinal and anteroposterior axes, as shown in portion (A) of Table 2. The combined 3D deviation was 2.2±0 8 mm on average with a maximum of 3.1 mm Variation (less than 2.3 mm on all three axes) was observed among individual IRRMs 160 mounted at different locations.

The variation may be due to the design of the IRRM 160 used in the PSS 100. Unlike commercial spherical reflective markers used in radiotherapy with other known systems, the specially-designed IRRM 160 in accordance with the invention has a flat round surface with a 6 mm diameter. The center-of-mass of the visible area of the IRRM 160 is identified as the marker location by the camera. Thus, orientation and curvature of the phantom surface where the IRRM 160 is mounted could affect its location as sensed by the cameras. Another factor contributing to variations among individual IRRMs 160 is the accuracy of IRRM 160 placement.

The IRRM 160 situated over chin area was selected in the remaining studies due to its superior visibility. In the end-to-end test, deviation with the IRRM 160 situated over chin area was 0.8 mm, 0.6 mm and 0.1 mm along lateral, longitudinal, and anteroposterior axis, respectively.

Portion (B) of Table 2 shows the difference between nominal couch shifts and PSS observed shifts. In this test, 12 combinations of 5 cm or 10 cm shifts were applied to the couch along each axis. Maximum difference on individual axis was less than 1.5 mm and maximum combined 3D difference was less than 2 mm. When there was a 60° couch rotation, maximum difference on individual axis and combined 3D difference increased to 2.7 mm (along anteroposterior axis) and 2.8 mm, respectively as shown in portion (C) of Table 2. A possible reason for the increased deviation with couch rotation is that the PSS 100 tracks IRRM 160 instead of the treatment isocenter. Small uncertainty in couch rotation can translate into large spatial deviation depending on the distance between the IRRM 160 and treatment isocenter. For example, a couch rotation error of 1° (typical uncertainty of couch rotation) results in an effective spatial displacement of 1.7 mm when the IRRM 160 is 10 cm away from the treatment isocenter.

The PSS 100 has been implemented in a plurality of treatment rooms. Setup of all patients in each treatment session is verified with the PSS 100. Ten patients with

TABLE 2

|  |  | ΔLAT (mm) | ΔLNG (mm) | ΔAP (mm) | ΔVECT (mm) |
|---|---|---|---|---|---|
| (A) N = 5 | mean ± SD | 1.1 ± 0.7 | 1.4 ± 0.8 | 1.0 ± 0.8 | 2.2 ± 0.8 |
|  | max (abs.) | 2.0 | 2.3 | 2.3 | 3.1 |
| (B) N = 12 | mean ± SD | 0.2 ± 0.2 | 0.5 ± 0.3 | 0.5 ± 0.3 | 0.8 ± 0.3 |
|  | max (abs.) | 0.5 | 1.2 | 1.0 | 1.6 |
| (C) N = 12 | mean ± SD | 0.7 ± 0.4 | 0.7 ± 0.5 | 1.3 ± 0.6 | 1.8 ± 0.6 |
|  | max (abs.) | 1.4 | 1.5 | 2.7 | 2.8 |

Abbreviations:
LAT: lateral dimension;
LNG: longitudinal dimension;
AP: anteroposterior direction;
VECT: 3D Vector;
SD: standard deviation Shown in Table 2 are system deviations (mean±standard deviation) in portion (A): the end-to-end test with individual disease in the H&N area were included in a retrospective study to evaluate accuracy of the PSS 100. The patients were immobilized with a H&N immobilization system such as the AccuFix™ H&N immobilization system by Q-Fix Systems LLC, of Avondale, Pa. The indexed immobilization system related CT BBs embedded in a top of the couch to the treatment isocenter through indexing bars. A couch indexing system (CIS) provided initial target localization, which was subsequently refined with in-treatment room CBCT guidance. The PSS 100 started automatic position verification at the moment the face mask was placed on the patient. Position deviations of the IRRM 160, observed with the PSS 100 before and after CBCT-guided couch adjustment, were used to evaluate system accuracy against the CBCT system and the CIS, respectively. Differences between PSS-observed couch shifts and couch shifts from CBCT registration were also reported.

The results of accuracy of the PSS 100, evaluated retrospectively on ten (10) H&N patients, are shown in Table 3.

TABLE 3

| N = 10 | | ΔLAT (mm) | ΔLNG (mm) | ΔAP (mm) | ΔVECT (mm) |
|---|---|---|---|---|---|
| (A) | mean ± SD | 1.8 ± 1.1 | 2.0 ± 1.0 | 1.5 ± 0.8 | 3.5 ± 0.6 |
|  | max (abs.) | 3.6 | 3.3 | 2.5 | 4.8 |
| (B) | mean ± SD | 2.2 ± 1.5 | 1.8 ± 1.7 | 2.1 ± 1.5 | 4.0 ± 1.8 |
|  | max (abs.) | 5.0 | 4.7 | 5.2 | 7.4 |
| (C) | mean ± SD | 2.6 ± 2.2 | 2.4 ± 1.6 | 3.2 ± 1.8 | 5.4 ± 1.9 |
|  | max (abs.) | 6.0 | 5.0 | 7.0 | 8.8 |
| (D) | mean ± SD | 0.5 ± 0.3 | 0.8 ± 0.5 | 0.7 ± 0.4 | 1.3 ± 0.3 |
|  | max (abs.) | 0.9 | 1.3 | 1.7 | 1.7 |

Abbreviations:
LAT: lateral dimension;
LNG: longitudinal dimension;
AP: anteroposterior direction;
VECT: 3D Vector;
SD: standard deviation System accuracy was retrospectively evaluated on ten (10) H&N patients. Shown in Table 3 are: (A) deviations with respect to the CIS, (B) deviations with respect to the CBCT system, (C) couch shifts determined by the CBCT system, and (D) residual errors of automatic couch motion observed by the PSS 100. Portions (A) and (B) of Table 3 show deviations of the PSS 100 with respect to the CBCT system and the CIS, respectively. The results shown in Table 3 were obtained by analyzing recorded real time IRRM 160 positions before and after CBCT-guided automatic couch shift. Mean deviation of the PSS 100 along each axis was less than 2.5 mm with respect to both systems, but the maximum deviation reached 3.6 mm (lateral direction) when compared with the CIS and 5.2 mm (anteroposterior direction) when compared with the CBCT system. A maximum combined 3D deviation of the PSS 100 was less than 8.0 mm when compared to both systems. The PSS 100 showed better agreement with the CIS than with the CBCT system. One reason is that, unlike the CBCT system, the PSS 100 and the CIS do not account for daily setup variation as well as patient internal anatomy change. For this reason, the CBCT system represents the desired treatment position and is used to guide treatment. Portions (C) and (D) of Table 3 show intended couch shifts based on CBCT image registration and residual errors as observed with the PSS 100, respectively. Intended couch shifts were evenly distributed among three axes with a mean between 2.4 mm and 3.2 mm, and a maximum between 5.0 mm and 7.0 mm Combined 3D shift had an average of 5.4 mm+1.9 mm, with a maximum of 8.8 mm Residual errors, observed with PSS 100, had an average less than 1.0 mm and a maximum less than 2.0 mm along all three axes. The maximum combined 3D residual error was less than 2 mm. These results show the ability of the PSS 100 in 1) predicting patient treatment position with sufficient accuracy and 2) accurately tracking automatic couch motion, which lacks independent verification in current practice.

For patients with disease in the thoracic or abdominal-pelvic region, the IRRM 160 is placed directly on the patient's chest or abdomen in a first treatment session. With the automated workflow, the IRRM 160 is transferred to the immobilization device. However, if it is desirable to continuously monitor the patient during treatment, or when the body mold is not used in patient treatment (e.g., for palliative purpose), the IRRM 160 could be affixed on the patient's skin in each session. Real-time position of the IRRM 160 is subject to breathing motion when directly placed on the patient's chest or abdomen. Maximum range of external surface motion can be over 20 mm depending on factors such as the patient's health condition and breathing pattern, which directly impacts action level selection in PSS 100. To evaluate the effect of breathing motion, ten patients with disease in the abdominalpelvic region were included in a study. The IRRM 160 was placed directly over the abdominal area where breathing motion mostly occurred. Motion range throughout the entire treatment session and accuracy of the PSS 100 when compared to the CBCT system and the CIS were reported for these patients.

Table 4 shows the results for abdominalpelvic patients.

TABLE 4

| N = 8 | | ΔLAT (mm) | ΔLNG (mm) | ΔAP (mm) | ΔVECT (mm) |
|---|---|---|---|---|---|
| (A) | mean ± SD | 2.5 ± 1.5 | 3.5 ± 1.5 | 3.2 ± 1.6 | 6.0 ± 1.2 |
|  | max (abs.) | 4.7 | 5.9 | 5.3 | 7.7 |
| (B) | mean ± SD | 3.5 ± 1.9 | 4.9 ± 2.4 | 2.7 ± 2.1 | 7.6 ± 1.8 |
|  | max (abs.) | 6.1 | 9.9 | 5.0 | 11.5 |
| (C) | mean ± SD | 3.0 ± 2.1 | 5.0 ± 4.3 | 1.8 ± 1.8 | 7.1 ± 3.4 |
|  | max (abs.) | 6.0 | 12.0 | 5.0 | 13.0 |

TABLE 4-continued

| N = 8 | | ΔLAT (mm) | ΔLNG (mm) | ΔAP (mm) | ΔVECT (mm) |
|---|---|---|---|---|---|
| (D) | mean ± SD | 0.9 ± 0.8 | 1.1 ± 0.7 | 1.7 ± 1.2 | 2.5 ± 1.1 |
|  | max (abs.) | 2.0 | 2.4 | 3.7 | 4.1 |
| (E) | mean ± SD | 1.2 ± 0.9 | 3.0 ± 1.3 | 9.0 ± 3.6 | 9.6 ± 3.7 |
|  | max (abs.) | 3.1 | 5.0 | 16.2 | 17.2 |

Abbreviations:
LAT: lateral dimension;
LNG: longitudinal dimension;
AP: anteroposterior direction;
VECT: 3D Vector;
SD: standard deviation System accuracy was retrospectively evaluated on ten abdominalpelvic patients. Shown in Table 4 are (A) deviations with respect to the CIS, (B) deviations with respect to the CBCT system, (C) couch shifts determined by the CBCT system, (D) residual errors of automatic couch motion observed by the PSS 100, and (E) patient motion range observed by the PSS. The IRRM 160 was placed directly on the patient's abdominal area in this study. Due to significant breathing motion, average IRRM 160 position of at least four breathing cycles (approximately 20 seconds) was used in the analysis. When compared with the CIS, average deviations were between 2.5 mm and 3.5 mm along all three axes, as shown in portion (A) of Table 4. Maximum deviations were less than 6.0 mm for each axis. Average deviations along each axis, in general, were 1 mm to 2 mm larger for these patients than for H&N patients. Although breathing motion partially contributed to these larger deviations, accuracy of the PSS 100 for these patients was mainly limited by accuracy in placing the IRRM 160 on a moving surface of the patient. Additional uncertainty of approximately 1 mm to 2 mm could have been introduced when placing the 6 mm diameter IRRM 160 over the tattoo on the patient's abdominal, compared to place an IRRM 160 on stationary face mask. Situated on loose skin, relative position of the tattoo with respect to treatment isocenter could vary from day to day, and from the time of CT simulation. Comparison of the PSS 100 with the CBCT system yielded similar results as shown in portion (B) of Table 4, except the maximum deviation along longitudinal direction, which was 4 mm larger. Portion (C) of Table 4 shows the intended couch shifts resulting from CBCT registration. These results were comparable to H&N patients along lateral and anteroposterior directions (see portion (C) of Table 3) but twice as large along longitudinal direction, with an average of 5.0 mm and a maximum of 12.0 mm Average residual errors of couch shift observed with the PSS 100, were below 2.0 mm for all three axes as shown in portion (D) of Table 4. A maximum difference of 3.7 mm was observed along anteroposterior direction. Portion (E) of Table 4 shows the range of patient motion, indicated by the motion of the IRRM 160. While the motion along either lateral or longitudinal direction was no more than 5.0 mm, average motion of 9.0±3 6 mm was observed along anteroposterior direction, with the maximum being 16.2 mm. The combined 3D motion had a maximum of 17.2 mm for these patients.

It has been demonstrated that the PSS 100 has adequate accuracy in detecting gross setup errors. The PSS 100 demonstrates good reproducibility, with short term and long term variation within 0.5 mm and 2 mm, respectively. An end-to-end test with an anthropomorphic head phantom revealed that the accuracy of the PSS 100 is about 1-2 mm when compared with CBCT. It accurately tracked couch motion of 5 cm or 10 cm along each axis to within 1.2 mm when there was no couch rotation, and within 2.7 mm when there was 60° couch rotation. These results show that the PSS 100 is able to accurately predict patient treatment position, and detect unintended couch shifts. With H&N patients, tracking accuracy of the PSS 100 slightly decreased due to finite CT slice thickness (3 mm), which affected POI identification of the CT BB in the TPS, and accuracy of IRRM 160 placement on a real patient. However, the accuracy was generally within 5.0 mm in each orthogonal direction when compared to both the CBCT system and the CIS, indicating that the PSS 100 is capable of detecting gross setup errors.

The feasibility of placing the IRRM 160 on abdominal area for abdominalpelvic patients has been investigated. Maximum deviation of the PSS 100 with respect to the CIS was less than 6.0 mm, but reached 9.9 mm when compared with the CBCT system. For the patients in this study, maximum daily CBCT shift along one direction was as high as 12.0 mm and patient breathing motion range reached 16.2 mm. These results have implication on an ability of the PSS 100 to detect gross setup errors (when defined as unintended shifts greater than 10 mm). The PSS 100 may generate frequent false alarms due to CBCT-determined large shifts or breathing motion for patients with heavy breathing. To alleviate false alarms resulting from large CBCT shifts, the action level needs to be relaxed, for example, to 15.0 mm along longitudinal direction. There are two methods to deal with false alarms resulting from large breathing motion. One method is to place the CT BB (and IRRM 160) on patient's chest area where less motion occurs. There are two issues with this method. First, it may require an extra skin tattoo on the patient at the time of CT scan, which means extra work in the workflow and potential source of error in IRRM 160 placement later at treatment. Second, the chest area may not be included in the CT scan for all abdominalpelvic patients. Another method is to permanently transfer IRRM 160 from the patient's skin to the immobilization device in the first treatment fraction. In this way, false alarms due to large breath motion can only occur in the first treatment session. With absolute deviations along each orthogonal direction shown together with an alarm to the therapist, it is easy to distinguish between false alarms and true setup errors. With this method, accidental couch movement can be detected in real-time. An advantage of this method is a streamlined, fully automated workflow. No therapist intervention is needed after the first treatment session.

A smooth clinic workflow is crucial for successful employment of a safety system on a large scale. Significant emphasis was placed on achieving a smooth clinic workflow in the development of the PSS 100. A streamlined workflow was achieved through synchronization with the R&V system 176 and mounting the specially-designed IRRM 160 directly on an immobilization device. The synchronization with the R&V system 176 allows for automatic loading of patient treatment information. The mounting the specially-designed IRRM 160 directly on the immobilization device enables immediate and automatic optical tracking. These automations not only minimize the workload of the therapist but also mitigate potential human errors in loading patient data or mounting the IRRM 160.

Setup related accidents typically do not occur in routine treatments, but occur in unexpected and unusual circumstances. Quality assurance and quality control systems are well designed to ensure patient safety in routine treatments; however, these systems may get bypassed under unexpected and unusual circumstances. For example, when treating a patient having diseases with a large lateral offset (>10 cm) from midline, collision between CBCT imaging source (or panel) and couch (or patient) may be inevitable. In these cases, CBCT imaging can only be performed with a lateral couch offset less than planned by a few centimeters (e.g., 5 cm). After CBCT imaging, the difference can be accounted for through manual couch adjustment. This process needs additional human involvement and can be error prone. As another example, if a posterior beam goes through metal component in the top of the couch, an unconventional indexing position may be necessary as a result of shifting the immobilization device longitudinally on the couch. If this information is not successfully communicated to substitute therapists in future treatment sessions, the patient 150 can be setup to a wrong longitudinal position. Similarly, when treating patients on a different LINAC than planned (due to, e.g., machine down) with different couch tops, different couch parameters are needed. The R&V system 176 provides the therapist the flexibility to override couch parameters at a treatment console without double approval. This can be a source of error if the wrong couch parameters are used for initial patient setup. As a final example, image-guided patient alignment using CBCT imaging or orthogonal filming may rely on image fusion of patient's bony structures (e.g., spine and femur); anatomical similarities of these bony structures along the longitudinal direction may lead to misregistration and become a source of error. Manual registration or automatic software registration using a smaller region of interest than desired can significantly increase the likelihood of such errors.

Some errors resulting from these unusual circumstances can be detected before treatment starts, at the expense of treatment delay and unnecessary imaging exposure to the patient 150; while some errors (e.g., inadvertent couch shift after imaging and incorrect image registration) can go undetected and lead to treatment of wrong sites. The PSS 100, which provides independent and continuous patient position verification, can detect all these unusual errors when it happens, thus avoiding unnecessary imaging exposure and preventing severe treatment errors. The PSS 100 is independent in the sense that it verifies patient setup by ensuring the position of the IRRM 160 relative to the isocenter of the treatment room. The PSS 100 is independent of treatment room, treatment machine, couch top design, immobilization device, and patient internal anatomy.

It has been demonstrated that the PSS 100 can catch potential gross setup errors, such as errors related to a couch indexing system. The PSS 100 can catch that the indexing bar for a H&V patient is placed at a wrong indexing hole (off by 7 cm) in CT scan, which would result in a wrongly calculated LINAC couch positions. This type of error can be caught by the PSS 100 before CBCT imaging, thereby preventing patients from unnecessary CBCT radiation exposure and potential treatment of the wrong sites.

An institution may have two machines each with couch tops that appear the same except that one couch top leads to a difference, e.g., 14 cm, in longitudinal couch parameter than the other machine for a same treatment. A patient is initially treated on a first machine. When the first machine breaks down, the patient may be treated on a second machine, and a difference between couch tops should be accounted for by creating setup beams with new couch parameters for the second machine. However, if setup beams for the first machine were accidentally loaded for patient setup on the second machine, there would be a 14 cm longitudinal offset in patient position. It has been demonstrated that the PSS 100 can catch this type of potential gross setup error before CBCT imaging.

A large (~1 cm laterally) couch adjustment may be needed after CBCT imaging. Due to concern of collision between gantry head and patient arms (such as a lung patient with arms up position), the couch may be arbitrarily moved laterally (~5 cm) such that the gantry head could go to intended treatment position. However, the couch may not be moved back as it should, and its parameters in the R&V system 176 may be overridden. It has been demonstrated that the PSS 100 can immediately catch the offset in patient position at time of couch shift before treatment. Without the PSS 100, this type of setup error could go undetected, i.e., not caught by the CBCT system, and result in treating a completely different site.

Instead of using a commercially available spherical IRRM 160, a flat-surfaced, disposable IRRM 160 is used with the PSS 100. The flat-surfaced, disposable IRRM 160 is easy to fabricate and mount. But the flat-surfaced, disposable IRRM 160 may be subject to a visibility issue due to its small volume and flat surface. The view of the cameras 121 and 122 can be obstructed by slope of patient's skin (in chest area) or when the IRRM 160 surface is angled away from the cameras. For a patient 150 treated with face mask, this potential problem is avoided by affixing the IRRM 160 over the patient's chin area and tilting the reflective surface toward the cameras. For a patient 150 treated with body mold, the IRRM 160 is shifted from the patient's skin onto a spot on the body mold. The flat surface of the IRRM 160 is tilted to ensure visibility. Another benefit of doing so is the streamlined workflow, but a tradeoff is a loss of an ability to track motion of the patient throughout the treatment. By mounting the IRRM 160 on the immobilization device instead of on the patient's skin for tracking, reproducibility of the patient 150 lying in the body mold is assumed. Reproducibility of the patient 150 lying in the body mold is ensured by aligning the two sets of skin tattoos (intended for correcting patient rotation) with marks on the body mold made at CT simulation.

To streamline clinic workflow, in one embodiment, the PSS 100 uses only one IRRM 160 for each patient 150. The results of using only one IRRM 160 for each patient 150 are: 1) the PSS 100 may lack sub-millimeter high precision, and 2) the PSS may not be able to distinguish translational and rotational errors in patient setup. However, neither of these results affects the ability of the PSS 100 to detect setup errors of more than 1 cm. Both translational error and rotational error lead to positional deviation of the IRRM 160 relative the isocenter of the treatment room, which triggers alarm in the PSS 100. These two types of errors can theoretically offset each other and mislead the PSS 100. However, the likelihood of such an event is low if the PSS 100 is only used as a complementary patient safety system to safeguard patient treatment, and not used to guide patient setup.

The PSS 100 can prevent gross setup errors in radiotherapy. The PSS 100 provides real-time independent position verification for the treatment of all disease sites based on optical-tracking technology, and is independent of treatment room, treatment machine, couch top design, immobilization device, and patient internal anatomy. The PSS 100 has been well-adopted into the use in a busy clinical environment because of its seamless workflow and effectiveness in catching setup errors. Because of its advantages of continuous tracking ability, no radiation dose, and fully automated clinic workflow, the PSS 100 is an ideal complement to complicated IGRT systems in ensuring patient safety in radiotherapy.

Figure 5:
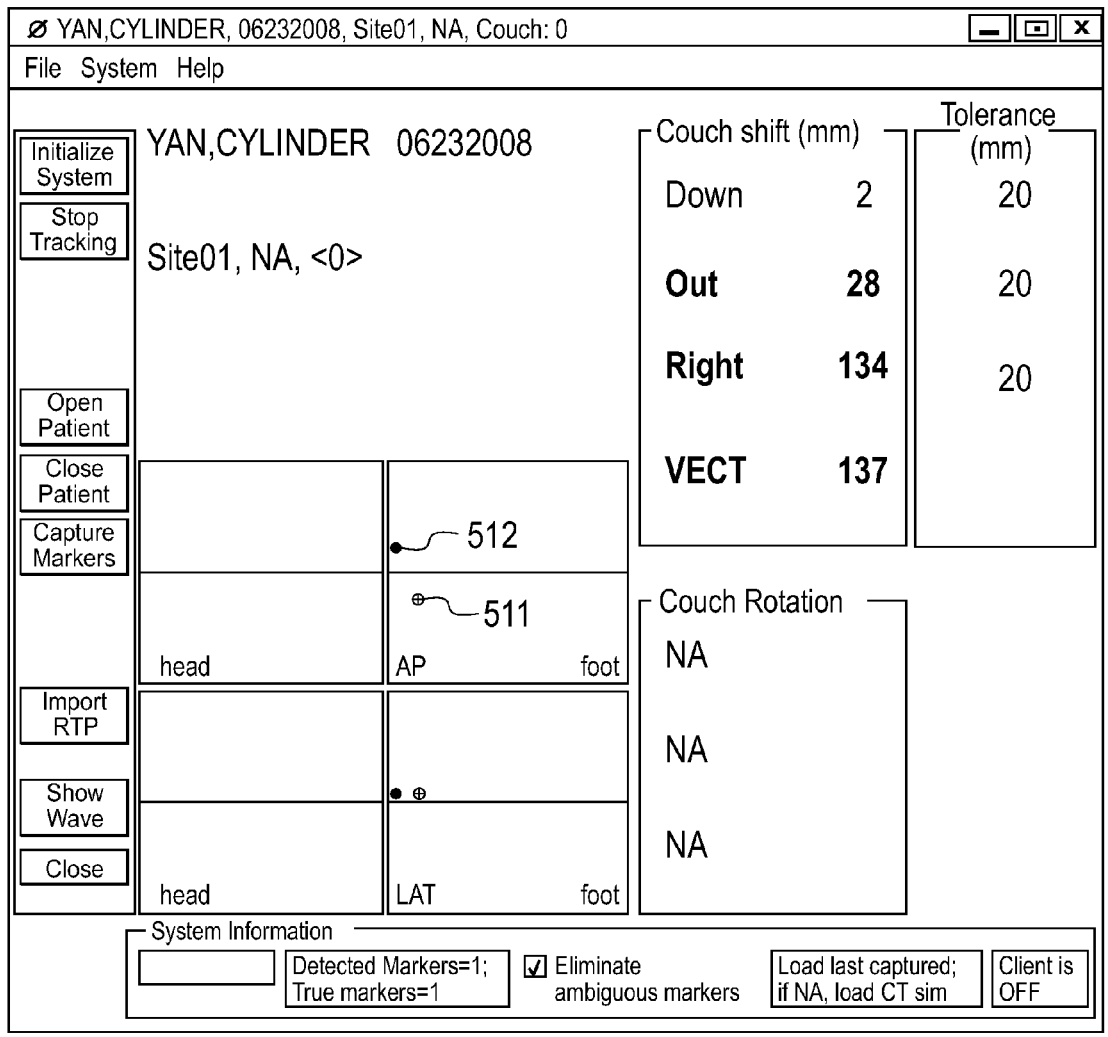
FIG. 5 is an illustration of one embodiment of a graphical user interface of the patient safety system, which is presented on the display shown in FIG. 1.

FIG. 5 is an illustration of one embodiment of the graphical user interface (GUI) 500 used with the PSS 100. In one embodiment, the GUI 500 is presented on the display 174. As described above, when a treatment beam is loaded in the R&V system 176, the PSS 100 retrieves patient name, field name and reference POIs from the database 212 of the PSS 100. At a top of the GUI 500 is shown patient's name and field name. In a bottom left portion of the GUI 500 are two image panels, one anteroposterior (AP) view and one lateral (LAT) view. When treating the patient 150, dots appear in the image panels of the GUI 500 representing predicted IRRM 160 position and observed real-time IRRM 160 position. Dots of a first type 511 (in one embodiment, in red color) represent reference markers. Dots of a second type 512 (in one embodiment, in green color) represent IRRMs sensed by the cameras 121 and 122. A difference between predicted and real-time IRRM 160 coordinates is shown in a top right portion (titled couch shift, measured in millimeter) of the display. The numbers are presented in a first manner (in one embodiment, in blue color) when they are within predefined threshold, and the numbers are presented in a second manner (in one embodiment, in red color) when they out of the predefined threshold. Couch rotation information is not used in the PSS 100.

Numbers on far right of the GUI 500 are tolerance values (in this example, "20, 20, 20"). When clinic values (in this example, "2, 28, 134") are within corresponding tolerance values, the clinic values are presented in a first manner (in one embodiment, in blue color). When clinic values (in this example, "2, 28, 134") exceed corresponding tolerance values, the clinic values are presented in a second manner (in one embodiment, in red color). Advantageously, an alarm is issued when clinic values exceed corresponding tolerance values. The alarm may include an audible alert, a visual alert, or both. Numbers in "Couch shift" column are deviations between the predicted IRRM 160 coordinates and the real-time IRRM 160 coordinates. In this example, the operator needs to move the couch down by 2 mm, out by 28 mm, and right by 134 mm to make the setup accurate. An intentionally wrong setup is shown in this example for pedagogical purposes.

The position sensor unit of the optical tracking system returns x y z coordinates of each IRRM 160. These are 3D objects, and they can be plotted in a way suitable for a particular application. In radiotherapy, AP and lateral (LAT) views of 3D objects are standard practice. The AP view is looking at the patient 150 from directly above the patient. The lateral view is looking at the patient 150 from patient's side.

The numbers are calculated based on x y z coordinates of the IRRM 160. There will be some deviation along each of the three dimensions (up-down, in-out, left-right). The graphics in the lower left portion of the GUI 500 are another way of showing these same deviations.

Numbers presented in the second manner (in one embodiment, in red color) mean the patient setup is out of tolerance. Numbers presented in the first manner (in one embodiment, in blue color) mean that the patient setup is within tolerance. One can specify different thresholds based on different clinic application and treatment sites, etc. For example, H&N sites are more rigid, and a smaller tolerance (e.g., 8 mm) is typically applied; pelvis area has more variations, and a large tolerance (approximately 10 mm) is typically applied.

The GUI 500 indicates a difference of location of the optically detected IRRM 160 and location of the reference, or predicted, IRRM 160 in three dimensions, which is a reason that numbers for "Down", "Out" and "Right" are presented. This information is convenient if the therapist needs to adjust the table. The GUI tells the therapist how to move the couch (direction and magnitude along each direction) to position the patient 150 accurately.

As described above, the therapist is alerted when exceeds the predefined threshold. However, there may be potential of delays in response by the therapist. An automatic treatment beam shutoff under this circumstance can truly safeguard the patient 150 from a wrong treatment. To safeguard the patient 150 from a wrong treatment, in one embodiment, the PSS 100 is coupled to the controller 105 of the LINAC 103. When a deviation between real-time coordinates of the IRRM 160 and predicted coordinates exceeds a predefined threshold (such as 1 cm), a signal is sent to the controller 105 of the LINAC 103 to cut off, i.e., to stop, the radiation of the treatment beam. A vector (VECT) value (see FIG. 5) is used to control the LINAC 103 in this regard. The VECT value is a quadrature sum of deviations along all three dimensions. Therefore, the VECT value is always larger than any of the other three deviations.

When treating patients with breath hold techniques, one or more IRRMs 160 can be placed over patient abdominal-pelvic area to monitor patient motion, and the treatment beam is turned on or off depending on motion of the one or more IRRMs 160. A portable display device, such as a tablet computer, can be connected to the computer 110 of the PSS 100 by wire or wirelessly, and is given to the patient 150. The patient 150 uses the portable display device as feedback to effectively hold his or her breath. Studies have shown audio or video feedback can significantly increase effectiveness and accuracy of gated treatment.

An active breathing coordinator device is used to assist patient breath hold through the use of a spirometer and a valve installed on a mouth piece. When the patient 150 is instructed to take a deep breath, the spirometer measures amount of air flowed into the patient's lung through the patient's mouth (nose clapped). When sufficient air has been inhaled, the patient 150 can shut down the valve to hold his or her breath. One or more IRRMs 160 can be placed on the patient's abdominalpelvic area to monitor the motion during patient breath hold. Reproducibility can be checked during multiple breath holds of same day or on different days.

After CBCT imaging and image fusion, the CBCT system generates required couch shifts to position the patient 150 at a desired position. To do this, automatic couch shifts can be conducted from the control room. With a single IRRM 160 mounted on patient immobilization device, the actual couch shifts observed by the PSS 100 can be used to quality control automatic couch shifts.

A single IRRM 160 can be mounted on a gantry head of the LINAC, on the CBCT system, or on an electrophoretic image display panel and on the couch. During the movement of these components, the PSS 100 can predict potential collisions between one and the other. For this purpose, a single IRRM 160 can be mounted on the patient's arms to protect them from collision.

A summary of most of the steps for a series of radiotherapy treatment sessions that are relevant to the PSS 100 is as follows. A therapist customizes an immobilization device (such as face mask or body mold, depending on tumor location) for the patient 150. The therapist makes marks on the patient's skin using a room laser as a reference. Solely for use with the PSS 100, an additional CT BB is placed on the patient's skin (or affixed to the immobilization device). The therapist performs a CT simulation scan. A CT image set is sent to the TPS. If CT BB was affixed to the immobilization device, the therapist replaces the CT BB with the IRRM 160; otherwise, a tattoo is made on the patient's skin at location of the CT BB. Next, a dosimetrist/physician designs a treatment plan in the TPS. The treatment plan is electronically sent from the TPS to the R&V system 176, and finalized by the dosimetrist. The CT BB is identified in the TPS as a POI and sent to a designated network place with a treatment isocenter for approval. An approved treatment plan is exported from the R&V system 176 to the same network place. Information exported from the TPS and the R&V system 176 at the designated network place is combined as patient tracking information and is imported into the database of the PSS 100. The patient 150 is expected to receive a plurality of radiotherapy treatment sessions, each radiotherapy session occurring on a different day, wherein all such days are subsequent to the day of the CT simulation scan. At a second session, and on each subsequent occasion that the patient 150 receives radiotherapy treatment, an IRRM 160 is affixed over the skin tattoo if the CT BB was placed on patient skin at CT simulation; otherwise, an IRRM is already affixed on the patient immobilization device. The therapist localizes the patient 150 using a skin mark or a couch index system. For this purpose, a setup beam is loaded in the R&V system 176. A local file for the PSS 100 is automatically created by the R&V system 176 when the setup beam is loaded. Every 2-3 seconds, the PSS 100 automatically scans a local folder for the local file created by the R&V system 176. The PSS 100 automatically loads relevant tracking information and starts optical tracking with the position sensor unit 104. A difference between detected IRRM position and reference position is shown in the GUI 500 on the display 174 and updated at a frequency of 15 Hz. Corrective action is taken if the difference exceeds a threshold. Patient localization is based on imaging (portal film or cone-beam CT). The patient (i.e., the couch) is shifted based on imaging and image registration. If the IRRM 160 was affixed on patient's skin, a suitable new location on the patient immobilization device is selected to permanently (throughout the course of radiotherapy treatment sessions) mount an IRRM. The new location of the IRRM 160 is captured by the PSS system 100. At this juncture, radiotherapy treatment of the patient 150 occurs. After the second session, the IRRM 160 is available with patient immobilization device, and tracking of the position of the patient 150 by the PSS 100 is fully automated.

As will be appreciated by one skilled in the art, aspects of the present invention may be embodied as a method, system or computer program product. Accordingly, aspects of the present invention may take the form of an entirely hardware embodiment, an entirely software embodiment (including firmware, resident software, micro-code, etc.) or an embodiment combining software and hardware aspects that may collectively be referred to as a "circuit," "module" or "system". Furthermore, aspects of the present invention may take the form of a computer program product embodied in one or more computer-readable medium(s) having computer-readable program code embodied thereon.

Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain, or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Computer program code embodied on a computer-readable signal medium may be transmitted using any appropriate medium, including but not limited to wireless, wireline, optical fiber cable, RF, etc., or any suitable combination of the foregoing.

The term "tangible computer-readable storage medium" includes, but is not limited to: solid-state memories such as a memory card that houses one or more read-only (non-volatile) memories, random access memories, or other re-writable (volatile) memories, a magneto-optical or optical medium such as a disk or tape, or other tangible media that can be used to store information. Accordingly, the disclosure is considered to include any one or more of a tangible computer-readable storage medium, as listed herein and including art-recognized equivalents and successor media, in which the software implementations herein are stored.

Computer program code, or computer program instructions, for carrying out operations for aspects of the present invention may be written in any combination of one or more programming languages, including an object oriented programming language such as Java, Smalltalk, C++ or the like, and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The computer program code, or computer program instructions, may also be stored in a computer-readable medium that can direct a computer, other programmable data processing apparatus, or other devices to function in a particular manner, such that the instructions stored in the computer-readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. The computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments, the methods described herein are intended for operation as software programs running on a computer processor. Furthermore, software implementations can include, but are not limited to, distributed processing or component/object distributed processing, parallel processing, or virtual machine processing, and can also be constructed to implement the methods described herein.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represents an example of the state of the art. Such standards are from time-to-time superseded by faster or more efficient equivalents having essentially the same functions. Wireless standards for device detection (e.g., RFID), for short-range communications (e.g., Bluetooth, WiFi, ZigBee), and for long-range communication (e.g., LTE) are contemplated for use by the computer 110.

The illustrations of examples described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. The examples herein are intended to cover any and all adaptations or variations of various embodiments. Combinations of the above embodiments, and other embodiments not specifically described herein, are contemplated herein.

The Abstract is provided with the understanding that it is not intended be used to interpret or limit the scope or meaning of the claims. In addition, in the foregoing Detailed Description, various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The terminology used herein is for the purpose of describing particular embodiments only and is not intended to be limiting of the invention. As used herein, the singular forms "a", "an" and "the" are intended to include the plural forms as well, unless the context clearly indicates otherwise. It should be understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "another", as used herein, is defined as at least a second or more. The terms "including" and "having," as used herein, are defined as comprising (i.e., open language). The term "coupled," as used herein, is defined as "connected," although not necessarily directly, and not necessarily mechanically. "Communicatively coupled" refers to coupling of components such that these components are able to communicate with one another through, for example, wired, wireless or other communications media. The term "communicatively coupled" or "communicatively coupling" includes, but is not limited to, communicating electronic control signals by which one element may direct or control another. The term "configured to" describes hardware, software or a combination of hardware and software that is adapted to, set up, arranged, built, composed, constructed, designed or that has any combination of these characteristics to carry out a given function. The term "adapted to" describes hardware, software or a combination of hardware and software that is capable of, able to accommodate, to make, or that is suitable to carry out a given function.

The terms "controller", "computer", "processor", "server", "client", "computer", "computer system", "personal computing system", or "processing system" describe examples of a suitably configured processing system adapted to implement one or more embodiments herein. Any suitably configured processing system is similarly able to be used by embodiments herein, for example and not for limitation, a personal computer, a laptop computer, a tablet computer, a smart phone, a personal digital assistant, a workstation, or the like. A processing system may include one or more processing systems or processors. A processing system can be realized in a centralized fashion in one processing system or in a distributed fashion where different elements are spread across several interconnected processing systems.

The terms "computer", "computer system", and "personal computing system", describe a processing system that includes a user interface and which is suitably configured and adapted to implement one or more embodiments of the present disclosure. The terms "network", "computer network", "computing network", and "communication network", describe examples of a collection of computers and devices interconnected by communications channels that facilitate communications among users and allows users to share resources. The terms "wireless network", "wireless communication network", and "wireless communication system" describe a network and system that communicatively couples computers and devices primarily or entirely by wireless communication media. The terms "wired network" and "wired communication network" similarly describe a network that communicatively couples computers and devices primarily or entirely by wired communication media.

The corresponding structures, materials, acts, and equivalents of all means or step plus function elements in the claims below are intended to include any structure, material, or act for performing the function in combination with other claimed elements as specifically claimed. The description herein has been given for purposes of illustration and description, but is not intended to be exhaustive or limited to the examples in the form disclosed. Many modifications and variations will be apparent to those of ordinary skill in the art without departing from the scope and spirit of the examples described or claimed. The disclosed embodiments were chosen and described in order to best explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

Unless stated otherwise, terms such as "first" and "second" are used to arbitrarily distinguish between the elements such terms describe. Thus, these terms are not necessarily intended to indicate temporal or other prioritization of such elements.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

What is claimed is:

1. A method, with a computer, of tracking changes in position of a patient while the patient is undergoing radiotherapy, comprising:
    placing a computed tomography ball bearing (CT BB) at a location on a surface of one of a face mask and an immobilization device for a patient;
    performing a treatment-simulation computed tomography scan of the patient;
    calculating, with a computer (110), coordinates of the CT BB, based on the treatment-simulation computed tomography scan of the patient;
    removing the CT BB from the surface of the one of a face mask and an immobilization device;
    placing an infra-red reflecting marker (IRRM) (160) at the location of the one of a face mask and an immobilization device;
    storing, in a database (212) communicatively coupled to the computer, the coordinates of the CT BB as predicted coordinates of a predicted location of the IRRM; and
    while the patient is receiving radiotherapy with a linear accelerator:
        determining a real-time location of the IRRM,
        comparing, with the computer, the real-time location of the IRRM with the predicted location of the IRRM, and
        displaying results of the comparing in a graphical user interface (500) of a display (174) communicatively coupled to the computer.

2. The method of claim 1, wherein the step of comparing continually compares the real-time location of the IRRM with the predicted location of the IRRM at a rate of 15 Hz, and wherein the step of displaying continually updates the results of the comparing at the rate of 15 Hz.

3. The method of claim 1, including the step of:
setting a tolerance for a deviation between the real-time location of the IRRM and the predicted location of the IRRM.

4. The method of claim 3, including the step of:
activating an alarm when the deviation between the real-time location of the IRRM and the predicted location of the IRRM is greater than the tolerance.

5. The method of claim 4, wherein the computer is communicatively coupled to the linear accelerator, and including the step of:
shutting off radiation from the linear accelerator when the deviation between the real-time location of the IRRM and the predicted location of the IRRM is greater than the tolerance.

6. The method of claim 3, wherein the computer is communicatively coupled to the linear accelerator, and including the step of:
shutting off radiation from the linear accelerator when the deviation between the real-time location of the IRRM and the predicted location of the IRRM is greater than the tolerance.

7. The method of claim 1, wherein the step of calculating uses a first coordinate system of the treatment-simulation computed tomography scan.

8. The method of claim 7, wherein the step of using includes using an optical tracking system (101), communicatively coupled to the computer, to optically determine real-time coordinates of the real-time location of the IRRM based on infra-red light reflections (123 and 125) from the IRRM sensed by cameras (121 and 122) of the optical tracking system, wherein the optical tracking system uses a second coordinate system.

9. The method of claim 8, including a step of converting the second coordinate system of the optical tracking system to the first coordinate system of the treatment-simulation computed tomography scan.

10. The method of claim 9, wherein the step of comparing includes comparing, with the computer, the real-time coordinates of the IRRM with the predicted coordinates of the IRRM.

11. The method of claim 10, wherein the step of comparing continually compares the real-time coordinates of the IRRM with the predicted coordinates of the IRRM at a rate of 15 Hz, and wherein the step of displaying continually updates the results of the comparing at the rate of 15 Hz.

12. The method of claim 11, including the step of:
defining a deviation between optically-determined real-time coordinates of the IRRM and the predicted coordinates of the IRRM as a quadrature sum of deviations along all three dimensions of the optically-determined real-time coordinates of the IRRM compared to the predicted coordinates of the IRRM.

13. The method of claim 12, including the step of:
setting a tolerance for the deviation between the optically-determined real-time coordinates of the IRRM and the predicted coordinates of the IRRM.

14. The method of claim 13, including the step of:
activating an alarm when the deviation is greater than the tolerance.

15. The method of claim 14, wherein the computer is communicatively coupled to the linear accelerator, and including the step of:
shutting off radiation from the linear accelerator when the deviation is greater than the tolerance.

16. The method of claim 13, wherein the computer is communicatively coupled to the linear accelerator, and including the step of:
shutting off radiation from the linear accelerator when the deviation is greater than the tolerance.

17. A method, with a computer, of tracking changes in position of a patient while the patient is undergoing radiotherapy, comprising:
placing a computed tomography ball bearing (CT BB) at a location on a surface of a patient;
performing a treatment-simulation computed tomography scan of the patient;
calculating, with a computer (110), coordinates of the CT BB, based on the treatment-simulation computed tomography scan of the patient;
removing the CT BB from the surface of the patient;
making a tattoo on skin of the patient at the location of the CT BB;
placing an infra-red reflecting marker (IRRM) (160) at the location of the tattoo;
storing, in a database (212) communicatively coupled to the computer, the coordinates of the CT BB as predicted coordinates of a predicted location of the IRRM; and
while the patient is receiving a first session of radiotherapy with a linear accelerator:
determining a real-time location of the IRRM,
comparing, with the computer, the real-time location of the IRRM with the predicted location of the IRRM, and
displaying results of the comparing in a graphical user interface (500) of a display (174) communicatively coupled to the computer.

18. The method of claim 17, including the steps of:
removing the IRRM from the location of the tattoo on the skin of the patient after completion of the first session of radiotherapy;
maintaining the tattoo on the skin of the patient until occurrence of at least one additional session of radiotherapy subsequent to the first session of radiotherapy; and
placing an IRRM at the location of the tattoo prior to start of the at least one additional session of radiotherapy.

19. The method of claim 18, including the step of retrieving, with the computer, from the database the coordinates of the CT BB as the predicted coordinates of the predicted location of the IRRM.

20. The method of claim 19, including, while the patient is receiving the at least one additional session of radiotherapy with the linear accelerator:
determining the real-time location of the IRRM,
comparing, with the computer, the real-time location of the IRRM with the predicted location of the IRRM, and
displaying results of the comparing in the graphical user interface of the display.

* * * * *